United States Patent
Vadrevu et al.

(10) Patent No.: US 11,351,245 B2
(45) Date of Patent: Jun. 7, 2022

(54) BUFFER FREE, ACID STABLE LOW DOSE VOLUME ROTAVIRUS VACCINE

(71) Applicant: Bharat Biotech International Limited, Hyderabad (IN)

(72) Inventors: Krishna Mohan Vadrevu, Hyderabad (IN); Sai Devarajulu Prasad, Hyderabad (IN); Krishna Murthy Ella, Hyderabad (IN)

(73) Assignee: Bharat Biotech International Limited, Hyderabad (IN)

( * ) Notice: Subject to any disclaimer, the term of this patent is extended or adjusted under 35 U.S.C. 154(b) by 0 days.

(21) Appl. No.: 16/310,039

(22) PCT Filed: Jun. 13, 2017

(86) PCT No.: PCT/IN2017/050237
§ 371 (c)(1),
(2) Date: Dec. 14, 2018

(87) PCT Pub. No.: WO2017/216808
PCT Pub. Date: Dec. 21, 2017

(65) Prior Publication Data
US 2019/0142932 A1    May 16, 2019

(30) Foreign Application Priority Data
Jun. 16, 2016  (IN) .............................. 201641020675

(51) Int. Cl.
| A61K 39/15 | (2006.01) |
| A61P 31/14 | (2006.01) |
| A61K 39/12 | (2006.01) |
| A61K 39/00 | (2006.01) |

(52) U.S. Cl.
CPC .............. *A61K 39/15* (2013.01); *A61K 39/12* (2013.01); *A61P 31/14* (2018.01); *A61K 2039/5254* (2013.01); *A61K 2039/542* (2013.01); *C12N 2720/12334* (2013.01)

(58) Field of Classification Search
None
See application file for complete search history.

(56) References Cited

U.S. PATENT DOCUMENTS 9,642,907 B2 *   5/2017  Ella ........................ A61P 31/14
2010/0068227 A1   3/2010  Ella

FOREIGN PATENT DOCUMENTS

| WO | WO/2007/132480 | 11/2007 |
| WO | WO2011/007363 | 1/2011 |
| WO | WO2013/160913 | 10/2013 |

OTHER PUBLICATIONS

PCT Search Report for Application No. PCT/IN2017/50237 dated Sep. 29, 2017.
PCT Written Opinion for Application No. PCT/IN2017/50237 dated Sep. 29, 2017.

* cited by examiner

*Primary Examiner* — Stacy B Chen
(74) *Attorney, Agent, or Firm* — Remenick PLLC

(57) ABSTRACT

A buffer free, acid stable, low dose volume rotavirus vaccine is disclosed. The vaccine is available in dose volume of less than 1 ml per dose for oral administration and it is without any buffer. The vaccine also does not require pre or post administration of any antacid at the time of oral administration of the vaccine to the subject to neutralize the stomach acid. The vaccine exemplifies nominal drop in vaccine titer at pH 2-4 for a time span of 30 minutes. The vaccine is stable at −20° C. for at least 60 months.

18 Claims, No Drawings

US 11,351,245 B2

BUFFER FREE, ACID STABLE LOW DOSE VOLUME ROTAVIRUS VACCINE

REFERENCE TO RELATED APPLICATIONS

This U.S. application is a National Stage submission under 35 U.S.C. § 371 of International Application No. PCT/IN2017/50237 filed Jun. 13, 2017, which claims priority to Indian Application No. 201641020675 filed Jun. 16, 2016, the entirety of each of which is incorporated by reference.

FIELD OF THE INVENTION

The invention relates to the field of rotavirus vaccines. More particularly, this invention relates to the field of rotavirus vaccines which are buffer-free or do not require any antacid pre, during or post administration of the rotavirus vaccine. This invention also relates to the field of amount of dose volume per unit vaccine, particularly rotavirus vaccines.

BACKGROUND OF THE INVENTION

It is well known that Rotaviruses are the leading cause of severe Gastroenteritis in infants and in children worldwide. Even improvements in hygiene, water quality and sanitation that may generally control many bacteria and parasites which are responsible for causing other types of diarrhea do not adequately prevent the spread of rotavirus. Therefore, vaccination is the only strategy capable of significantly reducing the disease burden caused by rotavirus infections in underdeveloped and developing countries across the globe. Vaccination is more significant for the countries which lack the required economic support and infrastructure to address the rotavirus infections in the infected patients. Till date, there have been at least four commercialized rotavirus vaccines in the world, the first among those being Rotashield® supplied by Wyeth Holdings, in the year 1999. This was a live, oral, tetravalent rotavirus vaccine produced using 1 rhesus monkey rotavirus, 3 rhesus-human reassortant viruses vaccine licensed in the United States. However, it was withdrawn from the market after 14 months because of its association with adverse affects of intussusception.

The Rotashield® comprised a composition containing, sucrose, monosodium glutamate, potassium monophosphate, potassium diphosphate, fetal bovine serum and neomycin sulphate in amphotericin medium. Corresponding patent publication on rotavirus vaccine compositions WO2000006196A2, teaches that the vaccine compositions may contain pharmaceutically acceptable auxiliary substances as required to approximate physiological conditions, such as pH adjusting and buffering agents and the like, for example, sodium acetate, sodium lactate, sodium chloride, potassium chloride, calcium chloride, sorbitan monolaurate, tri-ethanolamine oleate, citrate-bicarbonate, or the like. When the composition is administered orally it may also be necessary to provide the individual a buffer solution to partially neutralize stomach acid and protect the reassortant rotavirus while passing to the intestine. Buffer solutions appropriate for this use include sodium bicarbonate, citrate bicarbonate, or the like.

RotaTeq®, is a pentavalent human-bovine (WC3) reassortant live-attenuated, oral vaccine manufactured by Merck & Co., comprising a Bovine rotavirus strain WC3, P7[5]G6 involving 5 reassortants; out of which 4 reassortants with the VP7 gene from G1, G2, G3, or G4 and 1 reassortant with the VP4 P1A[8] gene from the human rotavirus parent strain with the remainder of the genes from the WC3 bovine rotavirus parent. The vaccine formulation (corresponding patent publications of Merck viz. WO1998/13065, WO2001/08495 and WO2002/011540) contains certain stabilizers in a tissue culture media along with the presence of buffers in the formulation itself, the said buffer being sodium citrate and sodium phosphate. The carboxylate of the patented claims are being used and acts as a buffer to make the rotavirus antigen withstand the stomach acidity while the virus antigen gets administered to the infant's stomach.

Further, Rotarix® is a monovalent vaccine, comprising a passaged Human rotavirus strain RIX4414 derived from the 89-12 strain. Rotarix® (produced by GlaxoSmithKline Biologicals), is a live vaccine that contains the attenuated monovalent G1, P[8] human rotavirus strain. The vaccine is available in lyophillized form mixed with stabilizers, to be reconstituted with a calcium carbonate based buffer diluent prior to vaccine administration into the subjects.

Rotarix was prepared by reconstituting the lyophilized active ingredient (RIX4414 strain+excipients) with 1.0 ml of GSK's $CaCO_3$ buffer contained in a pre-filled syringe. After injecting the buffer into the vial containing the lyophilized vaccine, the vial was shaken well to resuspend the vaccine. The entire volume of resuspended product was then withdrawn into the same syringe, the needle (or transfer device) of the syringe was discarded, and the product was administered promptly as a single oral dose. Alternatively, reconstitution of the commercial lyophilized vaccine will follow the same procedures, using an oral applicator filled with buffer and a transfer adapter instead of a syringe and needle. The reconstituted vaccine should appear milky white in appearance. It should be inspected visually for particulate matter and/or discoloration, and not be administered if either of these conditions exists. Rotarix is to be administered orally. The infant should be seated in a reclining position, and the entire content of the oral applicator containing the reconstituted vaccine should be administered on the inside of the cheek. Rotarix is not to be administered by injection. Hence, it is apparent that, reconstitution of buffer diluent contains so many steps, right from ensuring that the reconstitution has been properly done to the point of administration of the vaccine. All these factors definitely, cause decrease in vaccine compliance, amounting in partial protection from rotavirus infection rather than achieving a complete protection.

Corresponding patent applications from GSK on rotavirus vaccine formulations WO2001/012797, WO2005/02133, WO2006/087205, which involves a live attenuated rotavirus strain P43 serially passaged with specific mutations also supplemented with an antacid buffer for reconstitution. The said rotavirus strain G protein (VP4 and VP7) capable to induce immune response to at least 4 other rotavirus strains to G1 and at least one of G2 to G14 serotypes.

Other patented rotavirus vaccine compositions with stabilizers and buffers by Bharat Biotech International Limited with an Indian asymptomatic strain 116E isolated from a human child have also been disclosed. These require separate administration of an antacid buffer to the vaccine recipient prior to receiving the vaccine to increase the pH of the stomach, wherein the said antacid buffer is a citrate-phosphate buffer, in order to neutralize the stomach acidity at the time of administration of the rotavirus vaccine antigen. Patent Publication WO2013160913, provides rotavirus vaccine compositions comprising rotavirus antigens, stabilizers and certain novel buffer combinations. The buffers in the invention are pre-mixed in the rotavirus vaccine compositions to neutralize the high acidic pH of the stomach without, requiring separate administration of an antacid before vaccine administration.

Thus it is evident that different rotavirus vaccines have been developed using different strains, both human and animal reassortant types. There are a few important differences in characteristics of these strains, typical ones, as listed below.

TABLE 1

Differences between Human Monovalent and Animal reassortant vaccines

| Rotavirus vaccines with human strains | Animal reassortant rotavirus vaccines |
| --- | --- |
| Natural infection offers protection against subsequent rotavirus disease. | Animal rotaviruses are naturally attenuated strains, which lowers replication in humans. |
| Human viruses have high replication capacity in the host, and therefore attenuated by multiple tissue culture passage in multiple hosts. Since, these are human strains, a vaccine titer of 10^4 FFU/0.5 ml is enough to induce required immunogenecity against rotavirus infections in humans. | Rotavirus vaccines with animal reasssortant strians require very high vaccine titers to be able to induce the required immune response. |
| Broad immunity is acquired through various immune effector mechanisms. | Expectation that neutralizing antibody in the gut lumen is required. Immunity obtained is not high as vaccines with human strains. |
| Heterotypic protection is gained through broad immune response. This means, it offers cross protection across different strains. | Reassortant vaccine constructs to include the common human rotavirus antigens. |

Rationale Behind the Present Invention

Thus it is known that rotavirus is highly sensitive to acidic environments (Estes, M., Graham, D., Smith, E. and Gerba, C. (1979). Rotavirus Stability and Inactivation. *Journal of General Virology*, 43(2), pp. 403-409). It has also been reported that infantile gastroenteritis virus becomes unstable and there is a collapse of their outer shell and capsomeres when subjected to environment having pH less than 3.0 (Palmer, E., Martin, M. and Murphy, F. (1977). Morphology and Stability of Infantile Gastroenteritis Virus: Comparison with Reovirus and Bluetongue Virus. *Journal of General Virology*, 35(3), pp. 403-414). It has also been reported that many strains of rotavirus have been inactivated within a minute when exposed to environment having pH 2, and similar results were obtained with human gastric juice having pH 1.8 (Weiss, C. and Clark, H. (1985). Rapid Inactivation of Rotaviruses by Exposure to Acid Buffer or Acidic Gastric Juice. *Journal of General Virology*, 66(12), pp. 2725-2730). It has further been reported that human serotype 1 rotavirus is completely inactivated when subjected to an environment of pH 2.5 (Meng, Z., Birch, C., Heath, R. and Gust, I. (1987). Physicochemical Stability and Inactivation of Human and Simian Rotaviruses. *Applied and Environmental Microbiology*, 53(4), pp. 727-730). Rotavirus, in general, is known to be highly unstable when subjected to acidic environments and rapidly gets inactivated. Inactivation rates of three bovine and several primate-origin rotaviruses were determined during exposure to acid buffers at pH 2.0, pH 3.0 or pH 4.0. Each rotavirus was inactivated at pH 2.0 (the acidity most resembling the normal fasting stomach) very rapidly, with half-lives for infectivity determined to be 1 min or less. Each rotavirus was inactivated at a much slower rate at pH 3.0; inactivation at pH 4.0 was minimal. Some differences in acid resistance between different rotavirus strains were detected. Although these determinations were performed at room temperature (23° C.), experiments at diverse temperatures indicated an even more rapid rate of viral inactivation by acid at normal body temperature (37° C.). Studies of rotavirus exposed to natural human gastric juice at pH 1.8 or pH 2.1, revealed a rate of virus inactivation similar to that observed with glycine buffer of identical pH. (Ref: Geigy Scientific Tables, volume 1, 1981, page 126).

Rotavirus inactivation takes place between pH 2.0 to pH 3.0 but at pH 4.0 no or minimal inactivation takes place. Since, the stomach contains highly gastric acid environment, it has been imperative to add buffers into the rotavirus vaccine formulations till date, Buffers in rotavirus formulations aid in retaining a constant pH of the rotavirus vaccine formulations thus enabling antacid or buffering capacity of the vaccine formulations. The antacid capacity (also termed as acid neutralization capacity) of the rotavirus vaccines have been measured by Baby Rossett Rice Assays in the GSK's patents. The acid neutralization capacity of a given formulation is defined as the time measured to maintain the pH above 4.0 and is evaluated by Baby Rossette Rice assay. Baby Rosset assay reportedly is alleged to simulate the gastric environment of the human stomach. The latest patent by GSK U.S. Pat. No. 8,821,891B2 advocates for lower concentration of phosphates, and with an increased concentration of a carboxylate preferably adipate ranging from 100 mM to 1M, preferably 400 mM to 700 mM in a dose volume as low as 1.5 ml per human dose of rotavirus vaccine. Adipate acts as a buffer capable to withstand the high stomach acidity (pH 1 to 2). The capacity to withstand human stomach acidity is measured by Baby Rosset Rice Assay, having a value of 8 to 23 minutes which is said to be capable and good enough to avoid getting inactivation of the rotavirus antigen in the vaccine formulation after administration of the rotavirus vaccine into the human infant.

Thus, to effectively, administer a rotavirus vaccine which is capable to elicit immunogenic response sufficient enough to confer protection against rotavirus infections, at least 1.5 to 2 ml of the rotavirus vaccine or reconstituted vaccine formulation per human dose for oral administration is needed to effectively allow the rotavirus antigen to pass through the highly acidic environment of the stomach. Therefore, by the above descriptions of the status of the present nature of the rotavirus vaccines available till date, it would also be easily understood and acknowledged by the persons having skilled in the art, that rotavirus antigen is a highly acid labile antigen, and administration of rotavirus vaccine always requires an antacid or buffer component thereby increasing the required quantity (in terms of dosage in volumes per unit vaccine) of vaccine administration.

It is also a fact that the rotavirus antigen is a highly unstable virus and considering the situation that live attenuated rotavirus vaccine antigen would be more unstable; therefore the rotavirus antigen are being supplemented with respective proprietary vaccine stabilizers to stabilize the vaccine formulations, which add up to the amount of the vaccine dose in terms of volume per unit vaccine. Furthermore, inclusion of buffers or antacids or requiring reconstitution of the vaccine with a buffer based vaccine diluent increases the amount of vaccine dose in terms of volume per unit vaccine. Hence, providing a rotavirus vaccine without a buffer/antacid will definitely reduce the dosage volume per unit vaccine. At the same time, it is imperative that such a rotavirus vaccine without a buffer should not be compromising with the efficacy as well as stability of rotavirus vaccine.

Since, the subject of the rotavirus vaccine recipient is always an infant within the age group between 6 weeks to 6 months of age, there is every possibility that a considerable amount of rotavirus vaccine formulation delivered into the mouth of the infant gets spilled out. This creates a chance of partial administration of the vaccine thereby reducing vaccine compliance and not protecting the disease burden in spite of receiving the vaccine. Therefore, it is always desirable that the amount of dosage in terms of volume per unit rotavirus vaccine is reduced as much as possible without compromising the efficacy of the vaccine formulation. Currently the least dosage volume disclosed in the state of the art for rotavirus vaccine range from 1.5 ml-2.5 ml. The vaccines contain vaccine stabilizers and vaccine buffers adding up to the total vaccine dose volume. So, decrease in dosage volume per unit rotavirus vaccine having the same capacity to raise required immunogenicity for prophylaxis against rotavirus infections in infants will decrease the possibility of spilling out of the vaccine formulation administered to the infant. It would therefore be highly non-obvious to make available a low dose rotavirus vaccine formulation up to 1 ml, preferably only 0.8 ml, or most preferably 0.5 ml only per human dose without a buffer which is equally or rather, more effective than the rotavirus vaccine(s) made available with buffers or antacids having high dosage volume per unit vaccine.

The prior art discloses all rotavirus vaccine formulations all of which are to be stabilized in liquid formulations at refrigerated temperatures between 5±3° C. or as lyophillized powders which require reconstitution of the vaccine prior to the administration of the vaccine with a suitable diluent. It has been already discussed that, reconstitution of the vaccine for lyophillized powder require specific skill, and care. Further, separate manufacturing requirements for diluents along with the vaccine doubles the vaccine manufacturing costs as well as transportation costs. Deficiency in skill, care and appropriate infrastructure for warehouse requirements adds up to the problem with lyophillized rotavirus vaccine supply. For liquid vaccines at 5±3° C., the shelf life of the vaccines are limited to only up to 2 years. There is also an associated titer loss with vaccines made available at 2-8° C., during storage and transportation which is undesirable. But, rotavirus vaccine formulations at −20° C., it has been found that there has been no transportation and storage loss at all. The chances of vaccine contamination is also reduced to much greater extent for vaccines at −20° C. Further, the vaccine supply facility at −20° C. has been already established in almost 120 countries across the World for polio vaccine supplies. Therefore, according to existing facilities for vaccine storage and vaccine supplies similar to polio vaccine supplies would greatly help in reducing the rotavirus disease burden in the World. It is desirable that alternative strategies be developed wherein the rotavirus vaccine stability be further increased, so that the vaccine may be made available to remotest corners of the globe. Therefore, novel rotavirus vaccine formulations are being disclosed in this patent application, wherein the rotavirus vaccine formulations are stable for at least 5 years, being absolutely new and not stated in the current state of the art at all.

OBJECTIVE OF THE PRESENT INVENTION

The primary objective of the invention is to provide a buffer free and acid stable rotavirus vaccine.

One more primary objective of the invention is to provide a low dose volume up to 1 ml or even only 0.8 ml, preferably a 0.5 ml low dose volume rotavirus vaccine.

Another objective of the invention is to provide a stable rotavirus vaccine composition with vaccine volume of as low as 0.5 ml per dose.

Another objective of the invention is to reduce spilling out of rotavirus vaccine and minimizing associated vaccine wastage by the vaccine recipient and increase vaccine compliance thereby.

Another objective of the invention is to make a rotavirus vaccine composition that does not require any specific dilution or reconstitution techniques prior to or during vaccine administration.

One more objective of the invention is to provide a rotavirus vaccine which is stable for at least 5 years at −20° C.

A further objective of the invention is provide a low dose volume rotavirus vaccine which is stable for 2 years at 5±3° C., and 6 months at 25° C., and 1 week at 37° C.

One further objective of the invention is to provide a buffer free, low dose volume up to 1 ml rotavirus vaccine composition which is stable in stomach at pH 2 to pH 4 for at least 20 minutes.

Another objective of the invention is to provide a buffer free, low dose volume up to 1 ml rotavirus vaccine composition which is stable at acidic pH of 2-4 without any supplement of buffers or acid stabilizing agents.

A further objective of the invention is to provide a buffer free, acid stable, low dose volume rotavirus vaccine composition which does not require administration of any antacid or buffer, pre or post or during administration of the vaccine to the subject.

Alternatively, it is also an objective of the invention is to provide a low dose volume rotavirus vaccine of 0.5 ml along with the presence of a buffer, which is equally effective against rotavirus infections in humans.

Further objective of the invention is to provide a low dose volume rotavirus vaccine without a buffer, which is capable to generate either equivalent or greater immune response than rotavirus vaccines which are supplemented with antacids or buffers in vaccine compositions.

SUMMARY OF THE INVENTION

According to one embodiment of the invention provides a vaccine composition wherein the loss in rotavirus vaccine titer is not more than 0.55 FFU/per 0.5 ml between pH of 2-4 for a period of at least one hour.

In a further embodiment, the invention provides a vaccine composition wherein the loss in rotavirus vaccine titer is not more than 0.68 FFU/per 0.5 ml between pH of 2-4 for a period of at least 20 minutes.

One more embodiment of the invention, provides various rotavirus vaccine composition at a dose volume ranging from 1 ml to 0.5 ml, wherein the vaccine formulations are without any buffers or antacids, and exemplifies nominal drop in vaccine titer at pH 2 and pH for a time span of 30 minutes.

One another embodiment of the invention, provides acid neutralization capacities of a low dose volume rotavirus composition between 0.5 ml to 1 ml per unit vaccine in comparison with rotavirus vaccine compostions in presence of buffers established through Baby Rosset Rice assays.

A further embodiment of the invention, provides a buffer free rotavirus vaccine of dose volume only 0.5 ml which is capable to generate either equivalent or greater immune response in terms of four-fold seroconversion post vaccination similar to that of serconversion achieved with the vaccine formulation either in presence of buffers or administration of antacids.

In another embodiment, the invention provides a method of prophylaxis against rotaviral diarrhea in humans, the method comprising steps of administering an effective amount of a stabilized rotavirus vaccine formulation comprising rotavirus strain 116E, combination of sugars selected from sucrose, lactose and trehalose, lactalbumin hydrolysate, recombinant human serum albumin, without the presence of any buffer formulation in the said rotavirus vaccine formulation.

One more embodiment of the invention provides for stable rotavirus vaccine compositions, which are stable at −20° C. for at least 5 years.

A further embodiment of the invention provides stable rotavirus vaccine compositions at 2-8° C., 25° C. and 37° C. for 2 years, 6 months and 3 weeks respectively.

DETAILED DESCRIPTION OF THE INVENTION

Embodiment 1: Buffered Rotavirus Formulations and Gastric Acidity

It has been mentioned above in the background of the invention that, usage of buffers is a common practice rotavirus vaccine formulation strategies, that has being undertaken by various rotavirus vaccine manufacturers till date, and hence the Rota vaccine comprising the 116E strain at −20° C. formulation (SPG and DMEM) has been tested with citrate-bicarbonate buffer, and normal saline conditions initially.

Bharat Biotech International Limited obtained the human rotavirus strains 116E from National Institute of Health under a Material Transfer Agreement with National Institute of Allergy and Infectious Diseases (NIAID), NIH, Bethesda, USA. The complete genomic sequence of rotavirus strains 116E is already reported in literature.

Three Rotavirus vaccine formulations with rotavirus 116E stored at −20° C. were taken in 3 groups (Group I, II and III) as detailed below. The rotavirus vaccine compositions in all the three groups below comprise of live attenuated Rotavirus antigen of the strain 116E dissolved in 10% SPG (sucrose, potassium dihydrogen phosphate, and dipotassium hydrogen phosphate) and Dulbecco's Minimum Essential Medium. The said vaccine formulations were treated separately as detailed below:

Group I: 0.5 ml of Rotavirus 116 E formulation A at −20° C.

Group II: 2 ml (equivalent 4 human doses of 0.5 ml per human dose) of Rotavirus 116 E formulation A mixed with 5 ml of Normal Saline.

Group III: 0.570 ml of Rotavirus 116 E formulation A+mix of [1.42 ml Citrate–Bicarbonate buffer+8 ml of 34.8 mEq HCl].

As given above, Group I includes the rotavirus vaccine formulation at −20° C. wherein no buffer or saline was added to the vaccine formulation and the vaccine titer was measured for next 120 minutes. IN Group II, 2 ml of rotavirus 116E vaccine formulation (stored at −20° C.) was taken and added with 5 ml of normal saline, and vaccine titer was measured at a target titer of 10^6 FFU/ml up to 120 minutes. In Group III, 0.57 ml of rotavirus 116E vaccine formulation (stored at −20° C.) was taken and added with 1.42 ml of Citrate Bicarbonate Buffer and 8 ml of 34.8 mEq Hydrochloric acid.

TABLE 2

Rotavirus vaccine formulation (at storage temperature: −20° C.) vaccine titers in presence of buffers at 0 minute, 60 minutes and 120 minutes.

| Group# | 0 mins in FFU/0.5 ml | 60 mins in FFU/ml | 120 mins in FFU/ml | Remarks |
| --- | --- | --- | --- | --- |
| Group I | $10^{6.35}$ | $10^{6.17}$ | $10^{6.32}$ | Highly stable |
| Group II | $10^{5.76}$ | $10^{5.84}$ | $10^{5.69}$ | Fairly stable |
| Group III | $10^{4.61}$ | $10^{5.30}$ | $10^{5.11}$ | Fairly stable |

Therefore, the above table establishes that both for exposing the virus to normal saline conditions or in presence of buffer solutions, the rotavirus antigen titer is stable, and therefore the vaccine is stable.

Embodiment 2: Immunoperoxidase Assay of Rotavirus Vaccine Formulations at Different pHs Example 1

Immunoperoxidase Assay was done after subjecting the rotavirus vaccine formulations directly to the acidic environment by direct addition of the 34.8 mEq of Hydrochloric Acid (HCl) to the rotavirus vaccine formulation. The pH of the vaccine formulations were directly brought down from pH 7 to various lower pH values of pH 2, and pH 4 by direct addition of acid, and subsequently the vaccine antigen titer was measured at the given lower pH values of pH 2, and pH 4. Following this, the vaccine titer was measured for up to 1 hour at various lower pH of 2 and 4. Following observations were made. The reaction mixture was studied at various time points and various pH levels. Details are shown below in the table below. The said rotavirus vaccine formulations (at storage temperature −20° C.) contains live attenuated rotavirus antigen 116E, 10% SPG (sodium phosphate glutamate) dissolved in Dulbecco's Minimum Essential Medium.

TABLE 3

Immunoperoxidase Assay results at a target titer of 10^5.0 FFU/0.5 ml dose at 0 minutes and 60 minutes by direct addition of acid to rotavirus vaccine formulations (storage temperature: −20° C.).

| Sample details | Titer in FFU/0.5 mL dose | | | | | |
|---|---|---|---|---|---|---|
| | Actual titer at 0 minutes | Corrected Titer with Dilution Factor at 0 minutes | Actual titer after 1 hour | Corrected Titer with Dilution Factor after 1 hour | Log loss after 1 hour. | Remarks |
| 0.5 ml Rotavirus 116E vaccine formulation at pH 7.4 | $10^{4.95}$ | NA | $10^{4.94}$ | $10^{4.94}$ | — | — |
| 0.5 ml Rotavirus 116E vaccine formulation + 34.8 mEq HCl at pH 4.0 | $10^{3.58}$ | $10^{5.05}$ | $10^{3.58}$ | $10^{5.05}$ | Nil | No effect of pH |
| 0.5 ml Rotavirus 116E vaccine formulation + 34.8 mEq HCl at pH 2.0 | $10^{3.54}$ | $10^{5.01}$ | $10^{2.93}$ | $10^{4.40}$ | 0.55 | Marginal effect of pH |

Note: Calculated reduction in Infectivity Titer value due to dilution=$10^{1.47}$ FFU. Therefore actual vaccine titer after dilution is $10^{2.93}$ at pH 2. All the samples were titrated in triplicate by Immunoperoxidase Assay. The oral rotavirus vaccine (target titer $10^{5.0}$ FFU/0.5 mL) was stable at pH 4.0. Target Titer means, the minimum concentration of the rotavirus 116E antigen in the vaccine vial intended to be attained in the given vial. The original titer at neutral pH of the vaccine is $10^{4.95}$ FFU/0.5 ml at 0 minutes. The vaccine titer at pH 2 at 0 minutes is $10^{3.54}$ FFU/0.5 ml and the titer dropped to $10^{2.93}$ FFU/0.5 ml within 1 hour. So, after adding the dilution factor value of 1.47 due to addition of the acid, with the actual titer value ($10^{2.93}$ FFU/0.5 ml), the corrected vaccine titer at pH 2 after 1 hour from addition of the acid is $10^{4.40}$ as compared to the original vaccine titer of $10^{4.95}$ at pH 7 at 0 minutes. Therefore, the vaccine experienced a total log loss in vaccine titer of 0.55 only at pH 2.0 within a period of 1 hour. This establishes that, even at lower pH value of 2, that is to say in a specific acidic environment as it appears in the human stomach, the rotavirus vaccine formulation is capable to sustain its vaccine titer at a value of $10^{4.40}$ FFU/0.5 ml. At such vaccine titer, the vaccine is capable to raise sufficient immune response against subsequent rotavirus infections. In a clinical trial carried out with Rota 116E vaccine at a titre of $10^{4.0}$, the vaccine yielded a 4 fold sero-conversion around 62%, which is quite encouraging (Nita Bhandari et al, J Infect Dis 2009, 200, 421-9).

Example 2

The same experiment has been repeated with a different vaccine (at storage temperature −20° C.), wherein the target titer is 10^6.0 FFU/0.5 ml (dose) Calculated titer values along with dilution factor are provided in the following table at various pH values at 0 minutes and after 1 hour. The said rotavirus vaccine formulations (at storage temperature −20° C.) contains live attenuated rotavirus antigen 116E, 10% SPG dissolved in DMEM.

TABLE 4

Immunoperoxidase Assay results at a target titer of 10^6.0 FFU/0.5 ml dose at 0 minutes and 60 minutes by direct addition of acid to rotavirus vaccine formulations (storage temperature: −20° C.).

| Vaccine Sample Details | pH | 'Corrected Titer with Dilution Factor at 0' Hr in FFU/0.5 ml | Corrected Titer with Dilution Factor after 1 hour in FFU/0.5 ml | Log loss after 1 hour | Remarks |
|---|---|---|---|---|---|
| 0.5 ml Rotavirus 116E vaccine formulation | 7.2 | $10^{5.35}$ | $10^{5.30}$ | 0.05 (no loss) | No effect of pH |
| 0.5 ml Rotavirus 116E vaccine formulation + 34.8 mEq HCl | 4.0 | $10^{5.33}$ | $10^{5.09}$ | 0.24 (marginal loss) | No effect of pH |
| 0.5 ml Rotavirus 116E vaccine formulation + 34.8 mEq HCl | 2.0 | $10^{4.89}$ | $10^{4.21}$ | 0.68 (marginal loss) | Marginal effect of pH |

Conclusion: There was only loss in 0.24 log loss in vaccine titer in vaccine samples at pH 4.0, which is considered to be no effect on pH in practical circumstances kept for 1 hour. At pH 2.0, there was a 0.46 Log titer loss in the titer at 0 hour and a loss of 0.68 log 10 FFU at 1 hour. This is said to be having very marginal effect on pH on the vaccine titer values at such an acidic lower pH value of 2.

According to the above table, we see that vaccine titer of 10^4.89 FFU/0.5 ml at pH 2 is retained till a titer value of 10^4.21 FFU/0.5 ml; a log titer of 4.89-4.21 is good enough for replication of the rotavirus in the gut of an infant stomach at an age of 6 weeks to 2 years. The stomach acidity of an infant is also pH 2, representing a simulated gastric environment. The vaccine is still able to survive having a titer of 4.89 Log 10 FFU/0.5 ml, which is enough to cross the stomach and then get established into the intestinal villi and for further replication of rotavirus, responsible for generating immune response in the infant, thereby conferring protection and prevention of rotaviral gastroenteritis. Therefore, the vaccine was found to be stable at acidic pH of 2 for at least 1 hour duration without having any considerable loss in vaccine titer at all.

Embodiment 3: In Vitro Experiment to Demonstrate that Rotavirus 116E Vaccine does not Require Antacid Apart from the conclusions from the Clinical trial results that follow later in the patent specification, it was also proved in vitro simulating similar conditions of stomach acidity administering the vaccine directly without buffer.

Example 3.1

1 mL of vaccine (formulation 3A) containing rotavirus 116E, combination of sucrose (50%), lactose (0.5%) and trehalose (0.5%), lactalbumin hydrolysate (1%), human serum albumin (0.4%), was taken and added with 1.25 mL of 0.1 N HCl and mixed well. Sample was taken and tested for virus content at various pH levels at different time intervals. The results are shown in the table 5.1 below.

TABLE 5.1

Immunoperoxidase assay of 1 ml vaccine with rotavirus 116E (formulation 3A)

| S. No | Sample details | Virus content (FFU/mL) |
|---|---|---|
| 1 | pH 2.0-0 minutes | 5.72 |
| 2 | pH 2.0-10 minutes | 4.78 |
| 3 | pH 2.0-30 minutes | 3.84 |
| 4 | pH 3.0-0 minutes | 5.96 |
| 5 | pH 3.0-10 minutes | 5.96 |
| 6 | pH 3.0-30 minutes | 5.91 |
| 7 | Control | 6.10 |

Example 3.2

0.8 mL of vaccine containing rotavirus 116E, combination of sucrose (40%), and trehalose (0.5%), lactalbumin hydrolysate (20%), polyvinyl pyrollidine (0.5%) (formulation 3B) was taken and added with 1.25 mL of 0.1 N HCl and mixed well. Sample was taken and tested for virus content at various pH levels at different time intervals. The results are shown in the table 5.2 below.

TABLE 5.2

Immunoperoxidase assay of 0.8 ml vaccine with rotavirus 116E (formulation 3B)

| S. No | Sample details | Virus content (FFU/mL) | Virus content (FFU/0.8 mL) |
|---|---|---|---|
| 1 | pH 2.0-0 minutes | 4.71 | 4.62 |
| 2 | pH 2.0-10 minutes | 4.69 | 4.60 |
| 3 | pH 2.0-30 minutes | 4.41 | 4.32 |
| 4 | pH 3.0-0 minutes | 5.97 | 5.88 |
| 5 | pH 3.0-10 minutes | 5.94 | 5.85 |
| 6 | pH 3.0-30 minutes | 5.93 | 5.84 |
| 7 | Control | 6.10 | |

Example 3.3

0.5 mL of Rotavirus 116E vaccine containing combination of sucrose (60%), and trehalose (0.5%), soy protein (20%), pyridoxine-HCL (0.1%), polyvinyl pyrollidine (0.25%) (formulation 3C) was taken and added with 1.25 mL of 0.1 N HCl and mixed well. Sample was taken and tested for virus content at various pH levels at different time intervals. The results are shown in the table 5.3 below.

TABLE 5.3

Immunoperoxidase assay of 0.8 ml vaccine with rotavirus 116E (formulation 3C)

| S. No | Sample details | Virus content (FFU/0.5 mL) |
|---|---|---|
| 1 | pH 2.0-0 minutes | 4.29 |
| 2 | pH 2.0-10 minutes | 4.21 |
| 3 | pH 2.0-30 minutes | 3.39 |
| 4 | pH 3.0-0 minutes | 5.20 |
| 5 | pH 3.0-10 minutes | 5.17 |
| 6 | pH 3.0-30 minutes | 5.08 |
| 7 | Control | 5.80 |

Example 3.4

0.5 mL of Rotavirus 116E vaccine containing 10% SPG dissolved in DMEM (formulation 3D) was taken and added with 1.25 mL of 0.1 N HCl and mixed well. Sample was taken and tested for virus content at various pH levels at different time intervals. The results are shown in the table 5.4 below.

TABLE 5.4

Immunoperoxidase assay of 0.8 ml vaccine with rotavirus 116E (formulation 3D)

| S. No | Sample details | Virus content (FFU/0.5 mL) |
|---|---|---|
| 1 | pH 2.0-0 minutes | 4.78 |
| 2 | pH 2.0-10 minutes | 4.48 |
| 3 | pH 2.0-30 minutes | 4.29 |
| 4 | pH 3.0-0 minutes | 5.22 |
| 5 | pH 3.0-10 minutes | 5.17 |
| 6 | pH 3.0-30 minutes | 4.70 |
| 7 | Control | 5.80 |

Example 3.5

0.5 mL of Rotavirus 116E vaccine containing sucrose (40%), trehalose (0.5%), lactose (5%), rHSA (0.5%), LAH (1%) and mixed buffer (ammonium acetate+ammonium bicarbonate+diammonium orthophosphate) (formulation 3D) was taken and added with 1.25 mL of 0.1 N HCl and mixed well. Sample was taken and tested for virus content at various pH levels at different time intervals. The results are shown in the table 5.5 below.

TABLE 5.5

Immunoperoxidase assay of 0.8 ml vaccine with rotavirus 116E (formulation 3D)

| S. No | Sample details | Virus content (FFU/0.5 mL) |
|---|---|---|
| 1 | pH 2.0-0 minutes | 4.77 |
| 2 | pH 2.0-10 minutes | 4.65 |
| 3 | pH 2.0-30 minutes | 4.39 |
| 4 | pH 3.0-0 minutes | 5.21 |
| 5 | pH 3.0-10 minutes | 5.19 |
| 6 | pH 3.0-30 minutes | 4.87 |
| 7 | Control | 5.80 |

Conclusions: From the above tables it is evident that at pH 2.0 for 30 minutes also any Rotavirus 116E vaccine formulations are able to withstand in absence of any buffer or any antacid.

Embodiment 4: Baby Rossett Rice Analysis

BRR assay is the validated procedure for acid neutralization capacity of rotavirus vaccine formulations. So selected vaccine formulations containing Citrate Phosphate Buffer and Citrate Bicarbonate Buffer are evaluated for Acid Neutralization Capacity using this assay. In vitro experiments were conducted under simulated conditions of infantile stomach using Baby Rosette Rice Assay (BRR). Various formulations with various combinations of buffering agents were selected for the acid neutralization experiments and the results are given in the table below at various pH values wherein the conditions were simulated as infant stomach.

The vaccine formulations were diluted with water for injection up to 10 ml, then added 4 ml of 0.1 N HCl, then 0.5 ml of 0.1 N HCl added per minute until pH reaches 4.0. ANC is defined as the time in minutes taken to maintain the pH above 4.0.

TABLE 6

Details of Vaccine Formulations:

| Vaccine Formulation 4A | Rotavirus antigen 116E target titer of $10^6$ FFU/0.5 ml; 10% SPG, and DMEM (quantity sufficient) |
| Vaccine Formulation 4B | Rotavirus antigen 116E target titer of $10^6$ FFU/0.5 ml; 10% SPG, and DMEM (quantity sufficient) added to 2.5 ml of Citrate Bicarbonate Buffer |
| Vaccine Formulation 4C | Rotavirus antigen 116E target titer of $10^6$ FFU/0.5 ml, combination of atleast 2 Sugars (sucrose 50% and trehalose 0.5%) and Lactalbumin hydrolysate 0.5%. (Sample 8 below). |
| Vaccine Formulation 4D | Rotavirus antigen 116E target titer of $10^6$ FFU/0.5 ml, combination of atleast 2 sugars (Sucrose-40%, Trehalose-0.5%), 0.5% lactalbumin hydrolysate, 0.35% human serum albumin and 1.1M Phosphate Buffer. |

Following observations (Table 7) were made for Baby Rosset Rice assay performed with the vaccine formulations 4A to 4D listed above.

TABLE 7

Baby Rosset Rice analysis in comparison to rotavirus vaccine formulations with and without buffer.

| Vaccine Formulations | Initial pH | pH after addition of Acid | Volume of 0.1N HCl added | Baby Rosset Rice Assay Values | Initial Vaccine Titers in FFU/0.5 ml | Vaccine Titers in FFU/0.5 ml After 1 hour |
|---|---|---|---|---|---|---|
| Vaccine formulation 4A at −20° C. without buffer of 0.5 mL dose. | 7.48 | 1.95 | 4.0 mL | BRR of less than 0 minutes (immediate drop in pH) | $10^{4.83}$ | $10^{3.83}$ |
| Vaccine formulation 4B at −20° C. with 2.5 ml of citrate bicarbonate buffer of 0.5 mL dose. | 8.35 | 4.22 | 10.0 mL | BRR of 12 minutes | $10^{6.17}$ | $10^{6.15}$ |
| Vaccine formulation 4C at 5 ± 3° C. without buffer of 0.5 mL dose. | 7.28 | 3.98 | 5.0 mL | BRR of 2 minutes | $10^{5.30}$ | $10^{5.02}$ |
| Vaccine formulation 4D at 5 ± 3° C. with buffer of 1.5 mL or 2 mL dose. | 6.75 | 4.33 | 10.5 mL | BRR of approximately 13 minutes | $10^{6.12}$ | $10^{6.11}$ |

Conclusion: Therefore from the above table we find that, even if for the vaccine formulation 4A above which shows immediate drop from pH 7.48 to pH 1.95, the vaccine titer is retained from $10^{4.83}$ FFU/0.5 ml and $10^{3.83}$ FFU/0.5 ml. Same way, the vaccine titer is also retained in case of Vaccine formulation 4C between $10^{5.30}$ to $10^{5.02}$ FFU/

0.5 ml where the pH drops from 7.28 to pH of 3.98 within 2 minutes. Therefore, even if the BRR value is only 2 minutes, the vaccine titer is fairly retained i.e. 10^5.02 FFU/0.5 ml. This much amount of vaccine titer is enough for generation of immune response and thereby conferring protection and prevention of rotaviral gastroenteritis in human infants.

Embodiment 4: Clinical Trial without Buffer for ROTAVAC® Comprising Rotavirus 116E Strain Hypothesis and Study Rationale Natural transmission of rotavirus is assumed to occur via faecal-oral route. Rotaviruses in general are acid labile and it is believed that acidic environment affects the viability of the virus.

Given their acid-labile nature of rotaviruses, are so efficient in ubiquitously infecting mammals, most of which have gastric pH values around 2. One possibility is that the human infant stomach may be somewhat more permissive for survival of rotavirus than the adult stomach, as infant gastric pH levels tend to be approx. 3.2 compared with adults at approximately 1.0. This could account for the fact that 60 to 90% of reported human rotavirus disease occurs in children below the age of 3 years.

Study Design

In order to test this hypothesis a large multicenter randomized controlled trial was undertaken to evaluate and compare the vaccine immune response in subjects receiving ROTAVAC with citrate bicarbonate buffer to those who receive ROTAVAC without the buffer.

Accordingly, the study included the following three treatment groups:
Group I (received ROTAVAC® with 5 minutes prior administration of 2.5 ml of buffer),
Group II (received ROTAVAC® without buffer),
Group III (received ROTAVAC® immediately mixed with 2.5 ml of buffer prior to administration).

The study investigator and safety assessors (study coordinators) were blinded to the treatment group assignment. Blinding was achieved by a study nurse administering the vaccine as per the allocated treatment group. All subjects received 3 doses of the vaccine given 4 weeks apart. Vaccine immune response was tested 4 weeks after the third vaccine dose (day 84) and compared to baseline (day 0). Immunogenicity was tested in terms of Geometric Mean Titres (GMTs) of serum anti rotavirus IgA and seroconversion (fold rise in antibody levels from pre-vaccination to post vaccination) in the treatment groups.

Study Results and Conclusions

Post vaccination immune response was comparable with no statistically significant difference in the anti rotavirus IgA response between the treatment groups. Importantly, seroconversion and GMTs achieved in group II (ROTAVAC® administered without buffer) was similar to that in the other two treatment groups where ROTAVAC® was administered with buffer.

Post vaccination anti-rotavirus IgA GMTs in the group where ROTAVAC was administered without buffer was 20.7 U/mL in comparison to 19.6 U/mL and 19.2 U/mL in the two groups which received antacid buffer 5 minutes prior to vaccine and simultaneously mixed with vaccine respectively (Table 8). The differences between the groups were not statistically significant (p>0.05, Student's T-test).

TABLE 8

Geometric Mean Titres & 95% CI for results (day 0 & day 84)

| Visit | Group I (N = 290) | | Group II (N = 287) | | Group III (N = 286) | |
|---|---|---|---|---|---|---|
| | GMT | 95% CI | GMT | 95% CI | GMT | 95% CI |
| DAY0 | 10.5 | (9.4, 11.7) | 10.8 | (9.7, 11.9) | 10.2 | (9.2, 11.3) |
| DAY84 | 19.6 | (17.0, 22.7) | 20.7 | (17.9, 24.0) | 19.2 | (16.8, 22.1) |

N = Number of Subjects evaluated in each group;
GMT = Geometric Mean;
95% CI (LL, UL) = Confidence Intervals (Lower Limit, Upper Limit)

Similarly, the four-fold seroconversion observed in the groups that received ROTAVAC® without antacid buffer and with buffer was similar at 29.2%, 24.5% and 25.1% respectively (Table 9). Further, the lower limit of the 95% confidence interval of the difference of seroconversion (2-fold) between the treatment groups was >−10%, indicating non-inferiority in the immune response achieved with all three treatment regimens (table 10).

TABLE 9

Seroconversion and 95% CI (2, 3 or 4 fold change in antibody titres) between baseline and day 84 post-vaccination

| Fold Change | Group I (N = 290) | | Group II (N = 287) | | Group III (N = 286) | |
|---|---|---|---|---|---|---|
| | % | 95% CI | % | 95% CI | % | 95% CI |
| 2 | 30.7 | (25.7, 36.2) | 35.2 | (29.9, 40.9) | 33.5 | (28.3, 39.2) |
| 3 | 27.6 | (22.8, 33.1) | 32.4 | (27.3, 38.1) | 31.8 | (26.7, 37.4) |
| 4 | 24.5 | (19.8, 29.7) | 29.2 | (24.3, 34.8) | 25.1 | (20.5, 30.5) |

N = Number of subjects evaluated in each group;
(95% CI) = Confidence Intervals (Lower Limit, Upper Limit)

TABLE 10

Difference in % 2-fold seroconversion at post vaccination in the treatment groups % 2-fold Seroconversion post vaccination (day 84)

| | Group I (N = 290) | | Group II (N = 287) | | Group III (N = 286) | |
|---|---|---|---|---|---|---|
| | % | 95% CI | % | 95% CI | % | 95% CI |
| DAY 84 | 30.7 | (25.7, 36.2) | 35.2 | (29.9, 40.9) | 33.5 | (28.3, 39.2) |

Difference in % seroconversion with 95% CI 2-Sided, Chi-Square Test)

| Group | % (95% CI of difference) |
|---|---|
| Group I Vs Group II | 4.5 (−3.5, 12.5) |
| Group II Vs Group III | 1.6 (−6.5, 9.7) |
| Group I Vs Group III | 2.9 (−4.7, 10.5) |

The reactogenicity and safety with respect to solicited and unsolicited adverse events were comparable across the three groups with no statistically significant difference. ROTAVAC® vaccine was well tolerated in all three treatment groups that received the vaccine with or without the antacid buffer.

Embodiment 5: New Rotavirus 116E Formulations

Stability Data of ORV 116E Liquid Formulations at 37° C., 25° C. and 2-8° C.

The rotavirus vaccine formulations of a dose volume of 0.5 ml without buffer (samples 1 to 12, 14 to 16), and with mixed buffer at 0.5 ml dose volume (sample 13) have been examined for prolonged period of time ranging for a period up to 5 years, is provided below. The various formulation details is provided below along with their stabilites at 37° C. for up to 4 weeks, 25° C. for at least 6 months, and for 5±3° C. for up to 2 years to 5 years. The studies establish that, the rotavirus vaccine formulations without buffer at dose volumes of 0.5 ml are also stable in nature for prolonged periods of time at refrigerated temperatures for at least 2 years. Rotavirus vaccine formulations are also found to be stable for a period of 5 years at refrigerated temperatures as well.

Sample 1 is formulated containing rotavirus 116E, Sucrose 50%, Lactose 0.5%, HSA 0.5% and Lactalbumin hydrolysate 0.05%.

Stability of Sample 1:

| Temp | 0 day | 1 M | 2 M | 3 M | 6 M | 9 M | 12 M | 24 M | 36 M | 60 M |
|---|---|---|---|---|---|---|---|---|---|---|
| 5 ± 3° C. | 6.02 | 6.0 | | | 6.43 | | 6.21 | 6.16 | 6.16 | 6.07 |
| 25° C. | 6.02 | 6.07 | 5.81 | 5.9 | 5.51 | 4.65 | | | | |
| 37° C. | 6.02 | 5.32 | 2.63 | | | | | | | |

Sample 2 is formulated containing rotavirus 116E, Sucrose 50%, Trehalose 0.5%, HSA 0.5% and Lactalbumin hydrolysate 0.5%.

Stability of Sample 2:

| Temp | 0 day | 1 M | 2 M | 3 M | 6 M | 9 M | 12 M | 24 M | 36 M | 60 M |
|---|---|---|---|---|---|---|---|---|---|---|
| 5 ± 3° C. | 6.09 | 6.14 | | | 6.19 | | 6.07 | 6.10 | 6.05 | 6.01 |
| 25° C. | 6.09 | 6.02 | 6.06 | 5.63 | 5.51 | 2.48 | | | | |
| 37° C. | 6.09 | 5.47 | 3.23 | | | | | | | |

Sample 3 is formulated containing rotavirus 116E, Sucrose 50%, Trehalose 1.0%, HSA 0.5% and Lactalbumin hydrolysate 0.5%.

Stability of Sample 3:

| Temp | 0 day | 1 M | 2 M | 3 M | 6 M | 9 M | 12 M | 24 M | 36 M | 60 M |
|---|---|---|---|---|---|---|---|---|---|---|
| 5 ± 3° C. | 6.22 | 6.24 | | | 6.26 | | 6.14 | 6.20 | 6.13 | 6.04 |
| 25° C. | 6.22 | 6.18 | 6.15 | 5.80 | 5.34 | 2.03 | | | | |
| 37° C. | 6.22 | 5.35 | 3.22 | | | | | | | |

Sample 4 is formulated containing rotavirus 116E, Sucrose 40%, Lactose 0.5%, and Lactalbumin hydrolysate 1.0%.

Stability of Sample 4:

| Temp | 0 day | 1 M | 2 M | 3 M | 6 M | 9 M | 12 M | 15 M | 24 M | 60 M |
|---|---|---|---|---|---|---|---|---|---|---|
| 5 ± 3° C. | 6.19 | 6.18 | | | 6.08 | | 6.21 | 6.24 | 6.12 | |
| 25° C. | 6.19 | 5.66 | 5.10 | 4.8 | 3.01 | | | | | |
| 37° C. | 6.19 | 4.23 | 2.01 | | | | | | | |

Sample 5 is formulated containing rotavirus 116E, Sucrose 40%, Maltose 5.0% and Lactalbumin hydrolysate 1.0%.

Stability of Sample 5:

| Temp | 0 day | 1 M | 2 M | 3 M | 6 M | 9 M | 12 M | 15 M | 24 M | 60 M |
|---|---|---|---|---|---|---|---|---|---|---|
| 5 ± 3° C. | 6.35 | 6.37 | | | 6.18 | | 6.01 | 6.17 | 6.08 | |
| 25° C. | 6.35 | 5.89 | 5.11 | 4.77 | 2.43 | | | | | |
| 37° C. | 6.35 | 5.31 | 3.58 | | | | | | | |

Sample 6 is formulated containing rotavirus 116E, sucrose 40%, Trehalose 0.5% and lactalbumin hydrolysate 1%.
Stability of Sample 6:

| Temp | 0 day | 1 M | 2 M | 3 M | 6 M | 9 M | 12 M | 15 M | 24 M | 60 M |
|---|---|---|---|---|---|---|---|---|---|---|
| 5 ± 3° C. | 6.19 | 6.15 | | | 6.10 | | 6.03 | 6.22 | 6.13 | |
| 25° C. | 6.19 | 5.87 | 5.43 | 5.12 | 3.25 | | | | | |
| 37° C. | 6.19 | 4.02 | 2.52 | | | | | | | |

Sample 7 is formulated containing rotavirus 116E, Sucrose 40%, Trehalose 1.0% and Lactalbumin hydrolysate 1.0%.
Stability of Sample 7:

| Temp | 0 day | 1 M | 2 M | 3 M | 6 M | 9 M | 12 M | 15 M | 24 M | 60 M |
|---|---|---|---|---|---|---|---|---|---|---|
| 5 ± 3° C. | 6.34 | 5.79 | | | 6.00 | | 5.55 | 6.07 | 6.09 | |
| 25° C. | 6.34 | 6.07 | 5.81 | 5.9 | 5.51 | 4.65 | | | | |
| 37° C. | 6.34 | 5.32 | 2.63 | | | | | | | |

Sample 8 is formulated containing rotavirus 116E, sucrose 50%, Trehalose 0.5%, and lactalbumin hydrolysate 0.5%.
Stability of Sample 8:

| Temp | 0 day | 1 M | 2 M | 3 M | 6 M | 15 M | 18 M | 24 M | 36 M | 60 M |
|---|---|---|---|---|---|---|---|---|---|---|
| 5 ± 3° C. | 6.34 | 6.34 | | | 6.33 | 6.31 | 6.24 | 6.14 | 6.08 | |
| 25° C. | 6.34 | 6.32 | 6.14 | 6.01 | 5.25 | | | | | |
| 37° C. | 6.34 | 5.11 | 4 | | | | | | | |

Sample 9 is formulated containing rotavirus 116E, Sucrose 70%, Trehalose 0.5%.
Stability of Sample 9:

| Temp | 0 day | 1 M | 2 M | 3 M | 6 M | 15 M | 18 M | 24 M | 36 M | 60 M |
|---|---|---|---|---|---|---|---|---|---|---|
| 5 ± 3° C. | 6.38 | 6.31 | | | 6.23 | 6.44 | 6.35 | 6.26 | 6.18 | |
| 25° C. | 6.38 | 6.41 | 6.35 | 6.23 | 5.57 | | | | | |
| 37° C. | 6.38 | 5.07 | 4.01 | | | | | | | |

Sample 10 is formulated containing rotavirus 116E, Sucrose 50%, lactose 0.5%, Maltose 0.5%, HSA 0.5% and Lactalbumin hydrolysate 0.05%.
Stability of Sample 10:

| Temp | 0 day | 1 M | 2 M | 3 M | 6 M | 15 M | 18 M | 24 M | 36 M | 60 M |
|---|---|---|---|---|---|---|---|---|---|---|
| 5 ± 3° C. | 6.25 | 6.15 | | | 6.03 | 6.34 | 6.08 | 6.12 | 6.11 | 6 |
| 25° C. | 6.25 | 6.14 | 6.27 | 6.12 | 5.88 | | | | | |
| 37° C. | 6.25 | 5.02 | 4.35 | | | | | | | |

Sample 11 is formulated containing rotavirus 116E, Sucrose 50%, Trehalose 0.5%, maltose 0.5%, HSA 0.5%.

Stability of Sample 11:

| Temp | 0 day | 1 M | 2 M | 3 M | 6 M | 9 M | 12 M | 24 M | 36 M | 60 M |
|---|---|---|---|---|---|---|---|---|---|---|
| 5 ± 3° C. | 6.68 | 6.62 | 6.95 | 6.84 | 6.64 | 6.65 | 6.37 | 6.72 | 6.05 | |
| 25° C. | 6.68 | 6.50 | 6.20 | 6.04 | 5.32 | 4.47 | | | | |
| 37° C. | 6.68 | 6.10 | 5.58 | 4.26 | | | | | | |

Sample 12 is formulated containing rotavirus 116E, Sucrose 50%, Trehalose 0.5%, HSA 0.5% and Lactalbumin hydrolysate 0.05%.
Stability of Sample 12:

| Temp | 0 day | 1 M | 2 M | 3 M | 6 M | 9 M | 12 M | 24 M | 36 M | 60 M |
|---|---|---|---|---|---|---|---|---|---|---|
| 5 ± 3° C. | 6.62 | 6.76 | 6.98 | 7.00 | 6.86 | 6.74 | 5.99 | 6.46 | 6.17 | |
| 25° C. | 6.62 | 6.46 | 6.42 | 5.99 | 5.13 | 3.25 | | | | |
| 37° C. | 6.62 | 5.58 | 5.06 | | | | | | | |

Sample 13 is formulated containing rotavirus 116E, sucrose (40%), trehalose (0.5%), lactose (5%), rHSA (0.5%), LAH (1%) and mixed buffer (ammonium acetate+ammonium bicarbonate+diammonium orthophosphate).
Stability of Sample 13:

| Temp | 0 day | 1 M | 2 M | 3 M | 6 M | 9 M | 12 M | 24 M | 36 M | 60 M |
|---|---|---|---|---|---|---|---|---|---|---|
| 5 ± 3° C. | 6.61 | 6.59 | 6.58 | 6.60 | 6.53 | 6.54 | 6.18 | 6.01 | 5.83 | |
| 25° C. | 6.61 | 6.46 | 6.44 | 5.79 | 5.25 | 4.15 | | | | |
| 37° C. | 6.61 | 5.56 | 5.01 | | | | | | | |

Stability of Sample 13 at −20° C.:

| Temp | 0 day | 1 M | 2 M | 3 M | 6 M | 9 M | 12 M | 24 M | 36 M | 60 M |
|---|---|---|---|---|---|---|---|---|---|---|
| −20° C. | 6.61 | 6.59 | 6.59 | 6.56 | 6.54 | 6.52 | 6.21 | 6.11 | 6.13 | 6.09 |

Sample 14, 15 and 16 are formulated with rotavirus 116E, 10% SPG dissolved in DMEM. The samples 14, 15, and 16 are kept at −20° C., and stability checked for 60 months. The vaccine formulations 13, 14, and 15 are found to be very stable at −20° C. for a period of at least 5 years.

| Vaccine sample | 0 Day | 3 M | 6 M | 9 M | 12 M | 24 M | 36 M | 48 M | 60 M |
|---|---|---|---|---|---|---|---|---|---|
| Sample 14 (10^4.0 FFU/0.5 mL) | 4.25 | 4.01 | 4.08 | 4.15 | 4.25 | 4.02 | 4.18 | 4.12 | 4.08 |
| Sample 15 (10^5.0 FFU/0.5 mL) | 5.55 | 5.42 | 5.68 | 5.37 | 5.77 | 5.89 | 5.32 | 5.40 | 5.32 |
| Sample 16 (10^6.0 FFU/0.5 mL) | 6.12 | 6.12 | 6.06 | 6.33 | 6.36 | 6.27 | 6.15 | 6.11 | 6.05 |

Thus, it is established that various rotavirus vaccine compositions of 0.5 ml of dose volume are stable at −20° C. for 5 years, 2-8° C. for 2 years, 25° C. for 6 months, and 37° C. for 1 week. Irrespective of the vaccine formulation, the rotavirus vaccine at 0.5 ml to 1 ml dose volume is also found to be acid stable, as exemplified in embodiment 3 as well at a pH range of 2-4. Therefore, applicants wish to mention that irrespective of the vaccine composition details, any rotavirus vaccine comprising the live attenuated rotavirus 116E is capable to withstand the strong acidic environment in the human infant stomach and produce the required immune response against the rotavirus infections. The vaccine formulations presented in this patent application are only meant for the purposes of explaining the breadth and depth of the invention. It is impractical to provide all possible vaccine formulation details by the applicant, although the applicant has given numerous formulation strategies in Embodiment 3, Example 3 and Embodiment 5. Therefore, all possible obvious variations by a person skilled in the art for rotavirus vaccine formulation strategy comprising the rotavirus 116E strain are also covered under this invention. It is to be understood and accordingly construed that, the vaccine compositions which are not specifically included in this patent application comprising the live attenuated rotavirus 116E is also covered under the scope of this invention.

We claim:

1. A liquid rotavirus vaccine composition comprising:

a live attenuated rotavirus of strain 116E;

sucrose at a concentration of 50%;

lactose at a concentration of 0.5%;

lactalbumin hydrolysate at a concentration of 0.05%; and recombinant human serum albumin at a concentration of 0.5%;

wherein the composition contains no buffer or antacid, and wherein the composition has a dose volume of 0.5 ml.

2. The composition of claim 1, wherein the rotavirus has a titre of about $10^6$ FFU/0.5 ml.

3. The composition of claim 1, which can be maintained at from 2° C. to 8° C. for up to 12 months.

4. The composition of claim 1, which can be maintained at from 2° C. to 8° C. for up to 24 months.

5. The composition of claim 1, which can be maintained at from 2° C. to 8° C. for up to 36 months.

6. The composition of claim 1, which can be maintained at from 2° C. to 8° C. for up to 60 months.

7. A liquid rotavirus vaccine composition comprising:
   a live attenuated rotavirus of strain 116E;
   sucrose at a concentration of 50%;
   trehalose at a concentration of 0.5%;
   lactalbumin hydrolysate at a concentration of 0.5%; and
   recombinant human serum albumin at a concentration of 0.5%;
      wherein the composition contains no buffer or antacid, and
      wherein the composition has a dose volume of 0.5 ml.

8. The composition of claim 7, wherein the rotavirus has a titre of about $10^6$ FFU/0.5 ml.

9. The composition of claim 7, which can be maintained at from 2° C. to 8° C. for up to 12 months.

10. The composition of claim 7, which can be maintained at from 2° C. to 8° C. for up to 24 months.

11. The composition of claim 7, which can be maintained at from 2° C. to 8° C. for up to 36 months.

12. The composition of claim 7, which can be maintained at from 2° C. to 8° C. for up to 60 months.

13. A liquid rotavirus vaccine composition comprising:
    a live attenuated rotavirus of strain 116E;
    sucrose at a concentration of 50%;
    trehalose at a concentration of 1.0%;
    lactalbumin hydrolysate at a concentration of 0.5%; and
    recombinant human serum albumin at a concentration of 0.5%;
       wherein the composition contains no buffer or antacid, and
       wherein the composition has a dose volume of 0.5 ml.

14. The composition of claim 13, wherein the rotavirus has a titre of about $10^6$ FFU/0.5 ml.

15. The composition of claim 13, which can be maintained at from 2° C. to 8° C. for up to 12 months.

16. The composition of claim 13, which can be maintained at from 2° C. to 8° C. for up to 24 months.

17. The composition of claim 13, which can be maintained at from 2° C. to 8° C. for up to 36 months.

18. The composition of claim 13, which can be maintained at from 2° C. to 8° C. for up to 60 months.

* * * * *